United States Patent [19]

Metala et al.

[11] Patent Number: 5,029,476
[45] Date of Patent: Jul. 9, 1991

[54] ULTRASONIC SYSTEM FOR DETERMINING THE PROFILE OF SOLID BODIES

[75] Inventors: Michael J. Metala, Murrysville; Lee W. Burtner, Elizabeth Township, Allegheny County; Michael F. Fair, Oakmont, all of Pa.

[73] Assignee: Westinghouse Electric Corp., Pittsburgh, Pa.

[21] Appl. No.: 404,136

[22] Filed: Sep. 7, 1989

[51] Int. Cl.[5] ............................................. G01B 15/04
[52] U.S. Cl. ....................................... 73/620; 73/633; 367/99
[58] Field of Search ............. 73/1 DV, 597, 620, 633; 367/127, 99

[56] References Cited

U.S. PATENT DOCUMENTS

| | | | |
|---|---|---|---|
| 3,237,446 | 3/1966 | Wood | 73/620 |
| 3,287,963 | 11/1966 | Stanya et al. | 73/620 |
| 3,857,052 | 12/1974 | Beller | 73/620 |
| 4,238,844 | 12/1980 | Ueda et al. | 367/127 |
| 4,304,133 | 12/1981 | Feamster, III | 73/633 |
| 4,624,127 | 11/1986 | Narashima et al. | 73/1 DV |

FOREIGN PATENT DOCUMENTS 2033807  5/1980  United Kingdom ............... 367/127

Primary Examiner—Hezron E. Williams
Assistant Examiner—Rose M. Finley
Attorney, Agent, or Firm—M. G. Panian

[57] ABSTRACT

A system for determining the cross sectional profile of an object (24) having two opposed surfaces (26,28), includes:

an ultrasonic transducer (16) having a reference surface (20) and arranged to emit and receive ultrasonic energy via the reference surface (20);

a thickness determining unit (60) connected to the transducer (16) for causing the transducer (16) to emit ultrasonic energy via the reference surface (20) and for detecting reflected ultrasonic energy received by the transducer (16) via the reference surface (20) in order to derive indications of the distance between the reference surface (20) and an ultrasonic energy reflecting surface facing the reference surface (20);

a carriage (2) supporting the transducer (16);

a guide member (4) defining a linear travel path having a reference point and supporting the carriage (2) for movement along the travel path;

a position determining unit (12,44,62) operatively associated with the carriage (2) for deriving an indication of the location of the carriage (2) along the travel path relative to the reference point;

elements (32,34) for securing the guide member (4) to the object (24) so that the linear travel path extends along one of the two opposed surfaces (26); and a signal processing device (64) coupled to the thickness determining unit (60) and the position determining unit (12,44,62) for producing representations of the distance between the opposed surfaces (26,28) of the object (24) correlated with the location of the carriage (2) relative to the reference point when the reference surface (20) is in contact with one of the two opposed surfaces (26,28).

11 Claims, 2 Drawing Sheets

ULTRASONIC SYSTEM FOR DETERMINING THE PROFILE OF SOLID BODIES

BACKGROUND OF THE INVENTION

The present invention relates to the inspection of solid bodies, such as generator retaining rings, and particularly indirect determination of the profile of such a body along a given axis.

In industry, there is frequently a need to inspect machine parts which are subject to failure due to wear or other causes. For example, generator shaft retaining rings, which are mounted on the end of a generator shaft to retain windings in place, must be periodically inspected to identify any flaws which may have developed therein. The need to inspect such rings has gained increasing importance because the useful life of a large generator can depend on the condition of its retaining ring. Typically, cracks develop in the ring surface which contacts the generator windings, and these cracks frequently start at locations where a transition occurs in the inside diameter of the ring. If such cracks reach a critical size, the ring may rupture, resulting in the potential for extensive damage to the generator and surrounding equipment.

In order to forestall such an occurrence, many utilities perform periodic inspections of the generator retaining rings. The most common inspection method is an ultrasonic examination in which a high frequency ultrasonic signal is directed radially from the ring outer circumference toward the ring inner circumference. By monitoring the ultrasonic energy travel time, together with a precise knowledge of the ring profile, small cracks emanating from the inner circumference can be detected.

The success of such a procedure depends on an accurate knowledge of the ring profile, and such knowledge is not always available at the generator location. Removal of a ring to measure its profile is not acceptable for economic reasons and design drawings of the ring are not always available.

SUMMARY OF THE INVENTION

It is a primary object of the invention to determine the profile of an object, such as a generator retaining ring, without requiring removal of the object from its normal position.

Another object of the invention is to derive profile information in a rapid and simple manner by moving an ultrasonic transducer across one surface of the object whose profile is to be determined.

The above and other objects are achieved, according to the present invention, by: a system for determining the cross sectional profile of an object having two opposed surfaces, comprising: ultrasonic transducer means having a reference surface and arranged to emit and receive ultrasonic energy via the reference surface; thickness determining means connected to the transducer means for causing the transducer means to emit ultrasonic energy via the reference surface and for detecting reflected ultrasonic energy received by the transducer means via the reference surface in order to derive indications of the distance between the reference surface and an ultrasonic energy reflecting surface facing the reference surface; a carriage supporting the transducer means; guide means defining a linear travel path having a reference point and supporting the carriage for movement along the travel path; position determining means operatively associated with the carriage for deriving an indication of the location of the carriage along the travel path relative to the reference point; means for securing the guide means to the object so that the linear travel path extends along one of the two opposed surfaces; and signal processing means coupled to the thickness determining means and the position determining means for producing representations of the distance between the opposed surfaces of the object correlated with the location of the carriage relative to the reference point when the reference surface is in contact with one of the two opposed surfaces.

The objects according to the invention are further achieved by a method for determining the profile of an object having two opposed surfaces with the system described above, comprising: connecting the means for securing to the object so that the linear travel path extends parallel to one of the opposed surfaces of the object; moving the carriage along the travel path while operating the thickness determining means and the position determining means and maintaining the reference surface in contact with the one of the opposed surfaces; and operating the signal processing means for producing representations of the distance between the opposed surfaces along the travel path.

DESCRIPTION OF THE PREFERRED EMBODIMENTS

Figure 1:
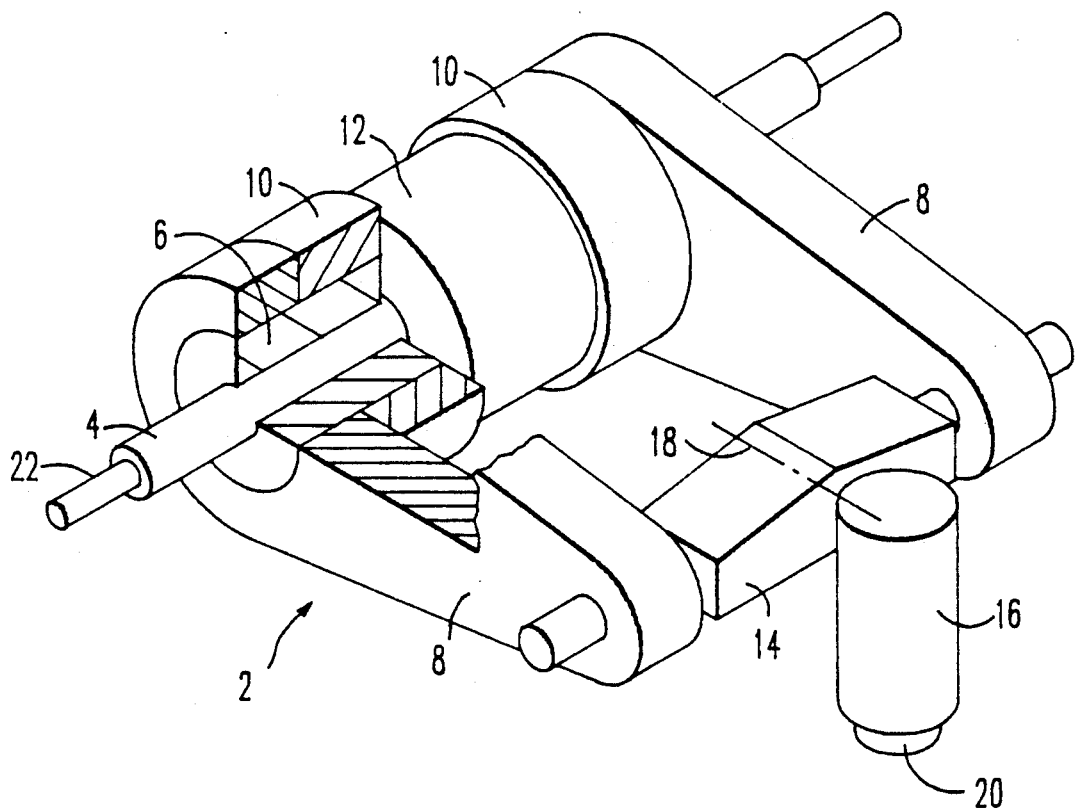
FIG. 1 is a perspective view of a thickness monitoring transducer assembly according to a preferred embodiment of the present invention.

The assembly shown in FIG. 1 is composed essentially of a carriage 2 slidably mounted on a guide tube 4 via bearings 6.

Carriage 2 is composed essentially of two arms 8 each mounted on a respective bearing 6 and each associated with a respective spacer 10. Secured between spacers 10 is a magnetic target 12 whose function will be described in greater detail below.

The free ends of arms 8 carry a transducer holder 14 which is mounted to arms 8 in such a manner as to be pivotal about an axis parallel to that of tube 4 while being fixed in position relative to arms 8 in the direction of the pivot axis. Holder 14 carries an ultrasonic transducer 16 in such a manner that transducer 16 is pivotal relative to holder 14 about an axis 18 which extends at a right angle to the pivot axis of holder 14.

Transducer 16 has a reference surface 20 which is to be maintained in contact with one surface of an object whose profile is to be determined.

Within tube 4 there is arranged an electromagnetic waveguide 22 through which electromagnetic energy can be propagated. Magnetic target 12 performs the function of reflecting at least a portion of such electromagnetic energy back toward the input end of waveguide 22 so that measurement of the travel time of such radiation along waveguide 22 can provide an indication of the position of carriage 2 along tube 4.

Figure 2:
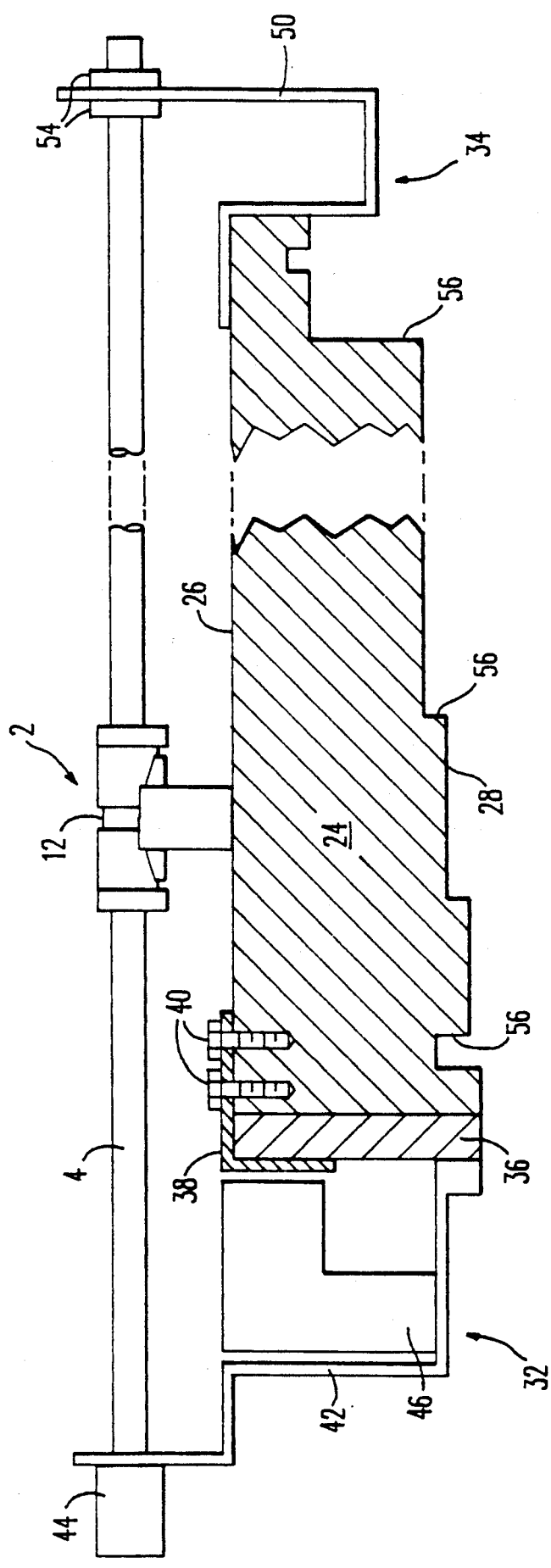
FIG. 2 is a side cross-sectional view of a measuring system according to the present invention including of FIG. 1.

A measuring arrangement according to the present invention incorporating carriage assembly 2 is shown in FIG. 2 in conjunction with an object 24 having two opposed surfaces 26 and 28 defining the object profile which is to be determined.

The object illustrated in FIG. 2 is a generator retaining ring having the characteristics described above. However, it will be appreciated that the system according to the invention can be employed to determine the profile of a wide variety of objects including, but not limited to, pipes, cylinders, plates, etc.

The system shown in FIG. 2 includes two support units 32 and 34 each arranged to be mounted at a respective axial end of body 24.

Support unit 32 includes a mounting plate 36 and a bracket 38 secured to plate 36. Bracket 38 can be secured to holes which may be provided in body 24 by pins or bolts 40. Secured to plate 36 is a support platform 42 which supports one end of tube 4 and a position transducer 44 operatively coupled to waveguide 22 (not visible in FIG. 2).

Platform 42 further carries a calibration block 46 having at least two regions with accurately determined thickness dimensions.

Support unit 34 may include a support member 50 which rests on surface 26 and on an associated axial end of object 24 and supports the other end of tube 4 with the aid of nuts or retaining rings 54.

The object 24 shown in FIG. 2, in a manner typical of generator retaining rings, has a generally cylindrical outer surface 26 and a stepped inner surface 28 possessing a number of diameter transitions 56.

Figure 3:
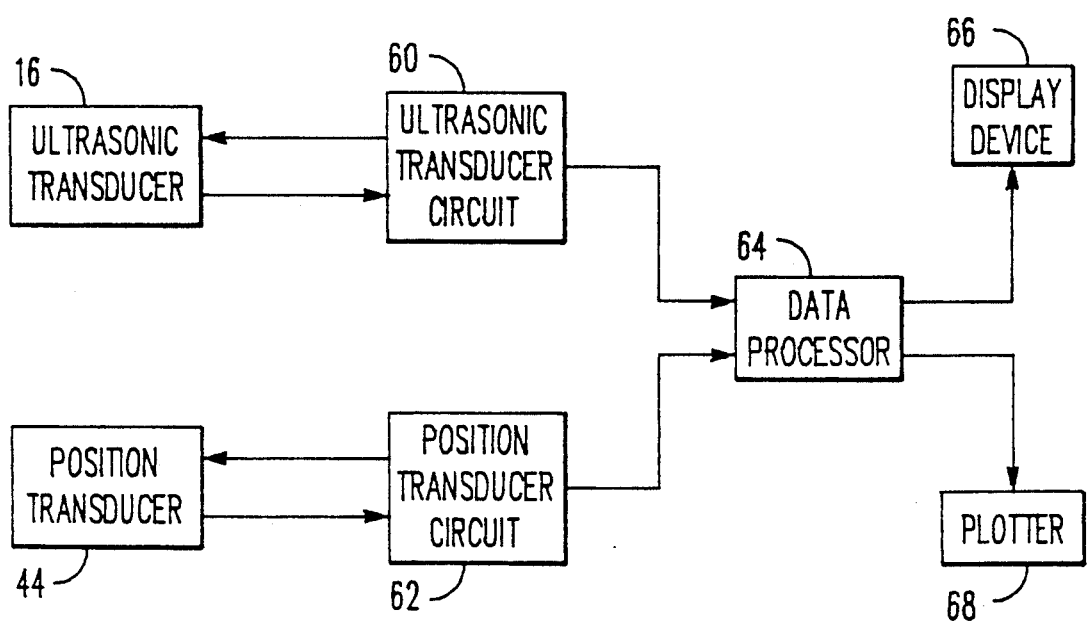
FIG. 3 is a block diagram of the circuit components of a measuring system according to the invention.

The circuit for deriving profile information according to the present invention is illustrated in FIG. 3 and includes an ultrasonic transducer circuit 60 coupled to supply signals to and recover signals from transducer 16 and a position transducer circuit 62 performing a similar function with respect to position transducer 44.

Circuit 60 derives, in a known manner, signals representative of the distance between surfaces 26 and 28 of object 24, i.e., the wall thickness of object 24, based on the travel time of ultrasonic energy to surface 28 and of reflected energy back to surface 26, while circuit 62 provides an output signal representative of the distance, along tube 4, between transducer 44 and target 12. Thus, the thickness signal generated at any given time at the output of circuit 60 will represent the thickness of object 24 at a location determined by the signal produced by circuit 62.

The measurement signals produced by circuits 60 and 62 are supplied to a data processor 64 which stores successively obtained thickness signals together with the associated position signals.

The resulting information can be processed, in a conventional manner, and supplied either to a display device 66 or a plotter 68 to produce a representation of the profile of object 24.

In order to generate a profile using the apparatus according to the present invention, this apparatus is mounted on object 24 whose profile is to be determined, as shown in FIG. 2. Then, with signals being supplied to and received from ultrasonic transducer 16 and position transducer 44, transducer 16 is moved along calibration block 46. Readings are taken from both regions of that block and circuit 60 is adjusted to display the correct thickness values. Then, using the transition from block 46 to plate 36 as a reference, and allowing for the thickness of plate 36, carriage 2 is moved along tube 4 while thickness readings are obtained. Reference surface 20 is maintained flush against outer surface 26 by an operator who grasps holder 14 and transducer 16 while manually moving carriage 2 along tube 4.

When circuit 60 produces an indication that a thickness transition has occurred, the operator will halt forward movement of carriage 2 and move transducer across the transition, producing a thickness indication and associated distance indication for each side of the transition.

This operation continues until the entire length of object 24 has been traversed.

At the end of such an operation, the resulting data can be assembled to produce a display or plot of the object profile.

While the device, as presently contemplated, is manually operated, it will be appreciated that the invention could be embodied in an automatic device in which carriage 2 is moved along tube 4 by a motor and holder 14 is configured to automatically maintain reference surface 20 against the object surface. With this arrangement, it would only be necessary to obtain thickness and position readings at regular intervals.

The resulting profile is then employed to determine the positions at which the object surface should be ultrasonically examined to locate crack formations.

While the description above refers to particular embodiments of the present invention, it will be understood that many modifications may be made without departing from the spirit thereof. In particular, any suitable distance measuring device can be used to provide indications of the position of carriage assembly 2 along tube 4. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed:

1. A system for determining the cross sectional profile of an object having two opposed surfaces comprising:

ultrasonic transducer means having a reference surface and arranged to emit and receive ultrasonic energy via said reference surface;

thickness determining means connected to said transducer means for causing said transducer means to emit ultrasonic energy via said reference surface and for detecting reflected ultrasonic energy received by said transducer means via said reference surface in order to derive indications of the distance between said reference surface and an ultrasonic energy reflecting surface facing said reference surface;

a carriage supporting said transducer means;

guide means defining a linear travel path having a reference point and supporting said carriage for movement along said travel path;

position determining means operatively associated with said carriage for deriving an indication of the location of said carriage along said travel path relative to said reference point;

means for securing said guide means to the object so that the linear travel path extends along one of the two opposed surfaces;

signal processing means coupled to said thickness determining means and said position determining means for producing representations of the distance between the opposed surfaces of the object correlated with the location of said carriage relative to said reference point when said reference surface is in contact with one of the two opposed surfaces; and a calibrating block carried by said means for securing at a location adjacent the object when said guide means are secured to the object, said calibrating block being disposed along said travel path to cooperate with said ultrasonic transducer means for allowing calibration of said thickness determining means.

2. A system as defined in claim 1 wherein said signal processing means comprises graphic display means for producing a display of/the profile of the object between the two opposed surfaces and parallel to the linear travel path.

3. A system as defined in claim 1 wherein said position determining means comprise: an electromagnetic wave transducer for emitting and receiving electromagnetic wave energy; electromagnetic wave propagating means coupled to said wave transducer for propagating wave energy along the linear travel path; and energy reflecting means mounted on said carriage and operatively associated with said propagating means for reflecting energy emitted by said wave transducer back to said wave transducer, whereby the time of travel of wave energy from said wave transducer to said reflecting means is proportional to the distance of said carriage from said reference point.

4. A system as defined in claim 3 wherein said propagating means comprises a waveguide, and said energy reflecting means produces a magnetic field which has a reflecting effect on energy propagated in said waveguide.

5. A system as defined in claim 1 further comprising orienting means connected between said carriage and said ultrasonic transducer means for allowing said reference surface to be maintained parallel to the one surface of the object when said guide means is secured to the object.

6. A system as defined in claim 5 wherein said guide means supports said carriage in a manner to permit said carriage to pivot about a first axis which extends along said linear travel path, and said orienting means comprises a mechanism for permitting said ultrasonic transducer means to pivot about a second axis parallel to the first axis and a third axis transverse to the second axis.

7. A system for determining the cross sectional profile of an object having two opposed surfaces comprising:

ultrasonic transducer means having a reference surface and arranged to emit and receive ultrasonic energy via said reference surface;

thickness determining means connected to said transducer means for causing said transducer means to emit ultrasonic energy via said reference surface and for detecting reflected ultrasonic energy received by said transducer means via said reference surface in order to derive indications of the distance between said reference surface and an ultrasonic energy reflecting surface facing said reference surface;

a carriage supporting said transducer means;

guide means defining a linear travel path having a reference point and supporting said carriage for movement along said travel path in a manner to permit said carriage to pivot about a first axis which extends along said linear travel path;

position determining means operatively associated with said carriage for deriving an indication of the location of said carriage along said travel path relative to said reference point, said position determining means comprising: an electromagnetic wave transducer for emitting and receiving electromagnetic wave energy; an electromagnetic waveguide coupled to said wave transducer for propagating wave energy along the linear travel path; and energy reflecting means mounted on said carriage and operatively associated with said waveguide for reflecting energy emitted by said wave transducer back to said wave transducer, said energy reflecting means producing a magnetic field which has a reflecting effect on energy propagated in said waveguide, whereby the time of travel of wave energy from said wave transducer to said reflecting means is proportional to the distance of said carriage from said reference point;

means for securing said guide means to the object so that the linear travel path extends along one of the two opposed surfaces;

orienting means connected between said carriage and said ultrasonic transducer means for allowing said reference surface to be maintained parallel to the one surface of the object when said guide means are secured to the object, said orienting means comprising a mechanism for permitting said ultrasonic transducer means to pivot about a second axis parallel to the first axis and a third axis transverse to the second axis;

signal processing means coupled to said thickness determining means and said position determining means for producing representations of the distance between the opposed surfaces of the object correlated with the location of said carriage relative to said reference point when said reference surface is in contact with one of the two opposed surfaces, wherein said signal processing means comprise graphic display means for producing a display of the profile of the object between the two opposed surfaces parallel to and the linear travel path; and a calibrating block carried by said means for securing at a location adjacent the object when said guide means are secured to the object, said calibrating block being disposed along said travel path to cooperate with said ultrasonic transducer means for allowing calibration of said thickness determining means.

8. A method for determining the profile of an object having two opposed surfaces with the system defined in claim 1, comprising:

connecting said means for securing to the object so that the linear travel path extends parallel to one of the opposed surfaces of the object;

moving said carriage along said travel path across said calibrating block and then across the object while operating said thickness determining means and said position determining means and maintaining said reference surface in contact with the one of the opposed surfaces; and operating said signal processing means for producing representations of the distance between the opposed surfaces along said travel path.

9. A method as defined in claim 8 wherein said step of moving is carried out manually.

10. A method as defined in claim 9 wherein said step of moving comprises stopping said carriage each time said thickness determining means indicates a change in the distance between the two opposed surfaces, and deriving an indication of the distance between the two opposed surfaces at each side of the location of the change.

11. A method as defined in claim 8 wherein said step of operating said signal processing means comprises: calibrating said thickness determining means while said transducer means are disposed adjacent said calibrating block.

* * * * *